US 6,666,895 B2

(12) United States Patent
Johnson et al.

(10) Patent No.: US 6,666,895 B2
(45) Date of Patent: Dec. 23, 2003

(54) PROSTHETIC LIMB GASKET

(75) Inventors: Christopher L. Johnson, Plainwell, MI (US); Lars Chrisman, Lawton, TX (US)

(73) Assignee: College Park Industries, Inc., Fraser, MI (US)

( * ) Notice: Subject to any disclaimer, the term of this patent is extended or adjusted under 35 U.S.C. 154(b) by 0 days.

(21) Appl. No.: 09/970,603

(22) Filed: Oct. 4, 2001

(65) Prior Publication Data

US 2002/0077703 A1 Jun. 20, 2002

Related U.S. Application Data

(60) Provisional application No. 60/237,859, filed on Oct. 4, 2000.

(51) Int. Cl.[7] ............................... A61F 2/66; A61F 2/78
(52) U.S. Cl. .......................................... 623/47; 623/53
(58) Field of Search ............................. 623/27, 35, 38, 623/47, 50, 52, 53

(56) References Cited

U.S. PATENT DOCUMENTS 4,938,775 A * 7/1990 Morgan ........................ 623/27
5,755,812 A * 5/1998 Becker et al. ................ 623/33

FOREIGN PATENT DOCUMENTS

RU 2066155 C1 * 9/1996 ............. A61F/2/60

* cited by examiner

Primary Examiner—David H. Willse
(74) Attorney, Agent, or Firm—Howard & Howard

(57) ABSTRACT

A prosthetic foot gasket for sealing between a foot shell covering a foot portion of an endoskeletal prosthetic leg and a leg portion thereof comprises a peripheral body having an upper surface and further defining a central opening therethrough. A lip extends from a bottom of the body and in combination with the body defines a groove therearound for receiving a top portion of the foot shell. A seal is affixed to an upper surface of the body for sealing engagement with the leg portion of the prosthetic leg.

4 Claims, 2 Drawing Sheets

PROSTHETIC LIMB GASKET

This application claims the benefits of Provisional application No. 60/237,859 filed on Oct. 4, 2000.

BACKGROUND

The present invention relates to a prosthetic foot apparatus and more particularly to a gasket cover surrounding an endoskeletal prosthetic foot apparatus.

Some modern prosthetic leg and feet apparatus consist of numerous metallic components connected together to simulate a human foot, ankle, and lower leg. The components primarily include a method of attaching a prosthetic foot to an endoskeletal pylon tube including several fasteners, bushings, and inserts providing the rotation, flexibility, and force bearing properties of the foot, ankle, and lower leg. Modern prosthetic feet have also evolved to include many complex components that are primarily covered by a foot shell, but they may be exposed at the top of the foot around the foot, ankle, and lower leg connection. Traditionally the endoskeletal leg, ankle, and foot components are covered by a cosmetic cover simulating the external look of a fall human leg. The cover is usually constructed of synthetic materials and connected to a socket at the top of the leg and to a top portion of the foot assembly. Creating the cover and connecting it to the socket and foot assemblies is often difficult and time consuming. The cover also reduces access to the components for making adjustments and performing maintenance.

More often, the modern endoskeletal apparatus is left uncovered. The endoskeletal components have become more socially acceptable to look at without a cover and thus the components have been left exposed. Leaving the components uncovered also allows for easy access to make adjustments or to perform maintenance. A problem with the uncovered components is that the components are subjected to the environment and often sustain damage and premature wear due to moisture, dust, dirt and other contaminants. Thus what is desired is an improved prosthetic foot & lower leg cover that is easily installed and removed and that provides protection of the endoskeletal components.

SUMMARY OF THE INVENTION

One aspect of the present invention is a prosthetic foot gasket for sealing between a foot shell covering a foot portion of an endoskeletal prosthetic leg and a leg portion thereof. The gasket comprises a peripheral body having an upper surface and further defining a central opening therethrough. A lip extends from a bottom of the body and in combination with the body defines a groove therearound for receiving a top portion of the foot shell. A seal is affixed to an upper surface of the body for sealing engagement with the leg portion of the prosthetic leg.

Another aspect of the present invention is a prosthetic leg comprising a leg portion and a foot and ankle portion affixed to a bottom of the leg portion. A foot shell covers the foot and ankle portion wherein the foot shell is made from a resilient material. A gasket is in sealing engagement with a top of the foot shell and extends to the leg portion wherein the gasket is also in sealing engagement with the leg portion.

These and other advantages of the invention will be further understood and appreciated by those skilled in the art by reference to the following written specification, claims, and appended drawings.

DETAILED DESCRIPTION OF THE PREFERRED EMBODIMENT

Figure 3:
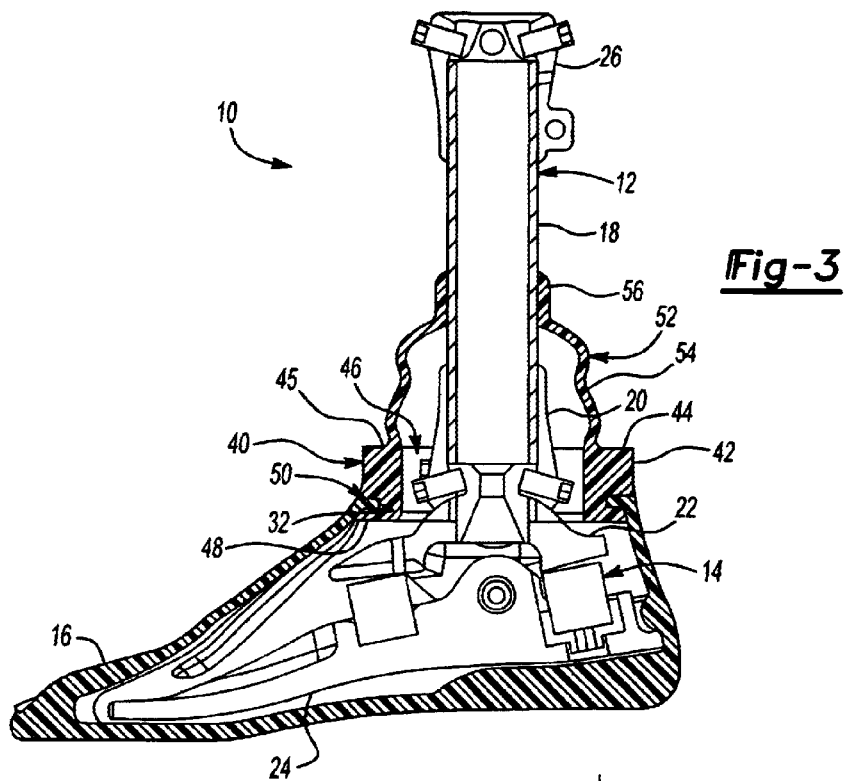
FIG. 3 is an elevational cross-section of the leg prosthesis and gasket of FIG. 2.

For purposes of description herein, the terms "upper", "lower", "left", "rear", "right", "front", "vertical", "horizontal", and derivatives thereof shall relate to the invention as oriented in FIG. 3. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
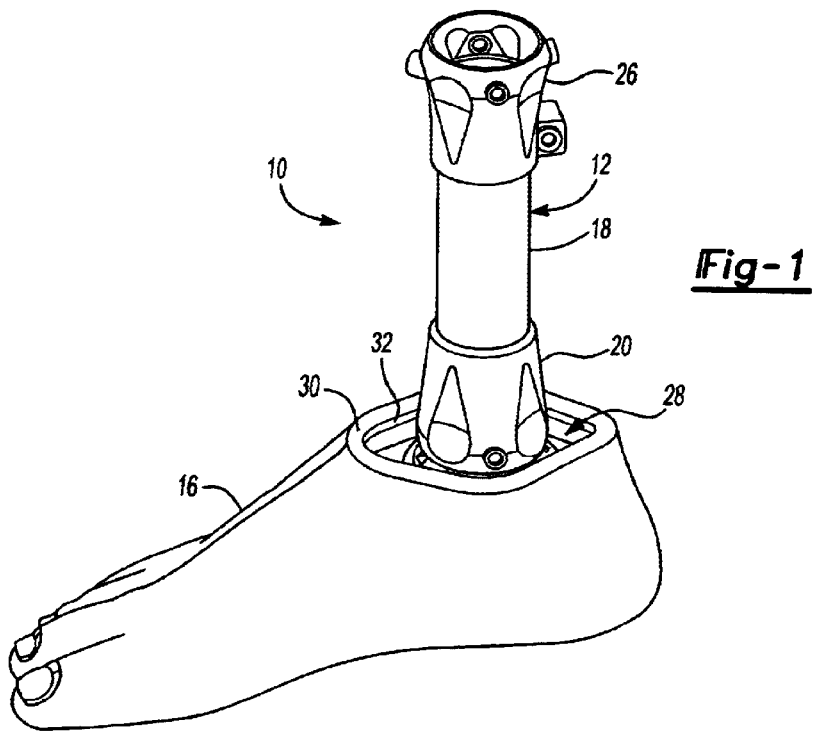
FIG. 1 is a perspective view of a representative endoskeletal leg and foot prosthesis showing foot shell covering the foot portion of the prosthesis.

Turning to the drawings, FIG. 1 shows a representative endoskeletal prosthetic leg 10. Endoskeletal prosthetic leg 10 generally comprises a leg portion 12 which has an endoskeletal tube 18 with a leg socket adapter 26 affixed to a top portion thereof and a tube adapter 20 affixed to a lower portion thereof. Socket adapter 26 attaches to a leg socket (not shown) which receives a user's leg therein. As shown in FIG. 3, tube adapter 20 is affixed to a foot and ankle portion 14. Foot and ankle portion 14 comprises an ankle 22 pivotally affixed to foot 24 such that tube adapter 20 is affixed to a top of ankle 22.

Referring again to FIG. 1, a foot shell 16 is received over foot and ankle portion 14 for cosmetic purposes. Foot shell 16 is generally shaped like a human foot and is molded from a flesh colored resilient material. Foot shell 16 has at an upper portion thereof a foot opening 28 for receiving the foot and ankle portion 14 therein. Foot shell 16 terminates at a top portion at an upper rim 30, which forms an upper peripheral lip 32 extending inwardly into foot opening 28. Foot opening 28 must be of sufficient size to receive therein foot and ankle portion 14 and thus when foot shell 16 is completely received over foot and ankle portion 14, foot opening 28 remains larger than leg portion 12 extending therethrough, and as here shown, specifically tube adapter 20. Such an arrangement permits the infusion of dirt, sand, and other contaminants, which are harmful to the functioning of foot and ankle portion 14.

Figure 2:
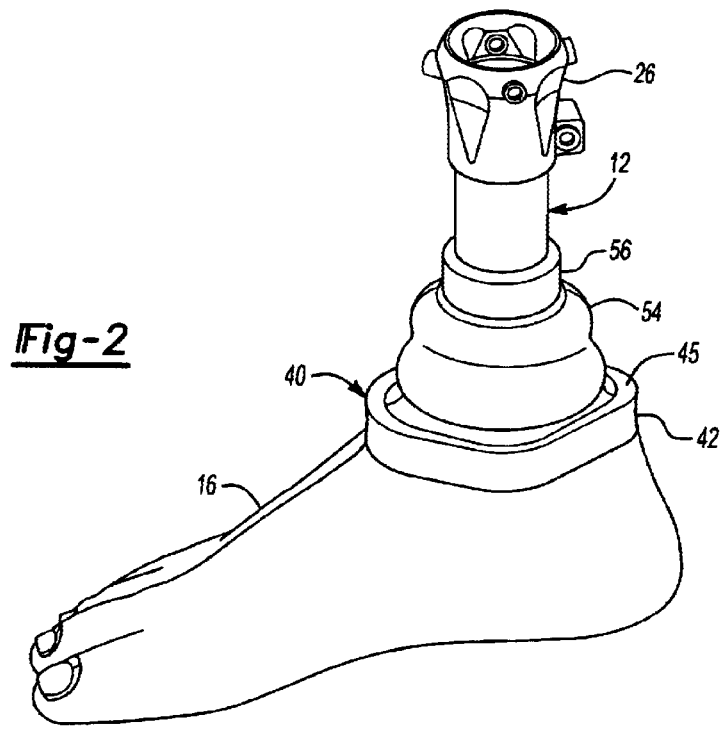
FIG. 2 is the endoskeletal leg prosthesis of FIG. 1 with a gasket according to the present invention installed thereon.

As shown in FIGS. 2–3, the exposed portion of foot opening 28 is covered with a foot gasket 40 embodying the present invention and illustrates its various components. Foot gasket 40 comprises a peripheral body 42 whose outer perimeter generally conforms to the shape of foot shell 16 at upper rim 30. Body 42 defines a central opening 46 for receiving leg portion 12 therein. A lip 48 extends from the bottom of body 42 and in combination with body 42 defines a groove 50, which extends around the periphery of body 42. Groove 50 is sized to receive therein lip 32 of foot shell 16 to seal gasket 40 with foot shell 16.

Foot gasket 40 has an upper surface 44 that has a seal 52 attached thereto. As shown in FIGS. 2–3 seal 52 comprises a hollow boot 54 surrounding the lower part of leg portion 12 and extending upward where seal 52 is terminated with seal ring 56. Hollow boot 54 and upper surface 44 form a shoulder 45 which can interface with a cosmetic leg cover. Seal ring 56 is sized to closely receive endoskeletal tube 18 therein, thus completing gasket 40 and sealing the interior of foot shell 16 so that contaminants do not enter and impair the function of foot and ankle portion 14. Gasket 40 is constructed of a resilient material, which is resiliently deformable so that the gasket 40 can easily be installed and maneuvered to receive lip 32 in groove 50.

Figure 4:
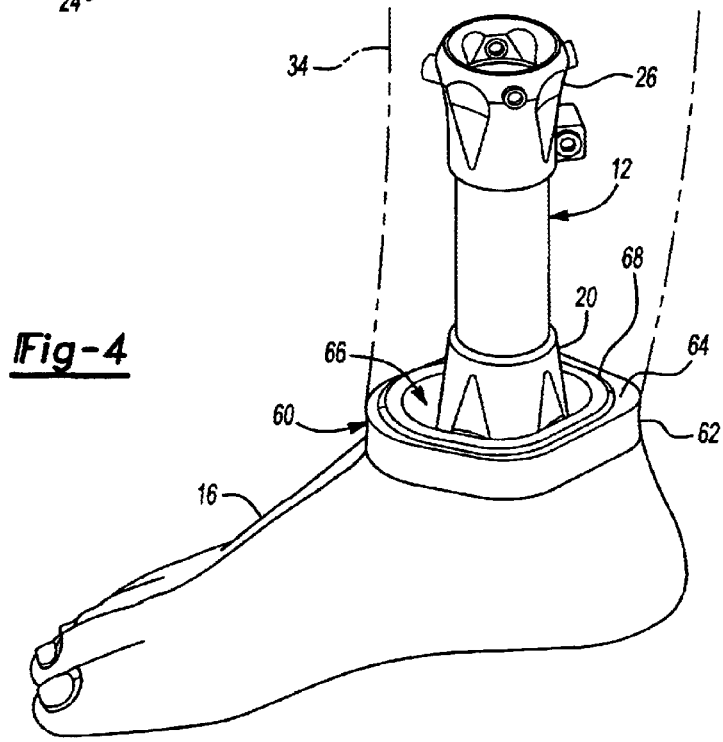
FIG. 4 is a perspective view of the endoskeletal leg prosthesis wherein an upper surface of the gasket is adapted for bonding to a cosmetic leg covering.

FIG. 4 shows alternative embodiment gasket 60 wherein gasket 60 comprises a body 62 constructed similarly to body 42 in the previous embodiment such that gasket 60 affixes to foot shell 16 in a like manner. Gasket 60 defines a central opening 66 for receiving leg portion 12 therein and terminates at top surface 64. Adhesive layer 68 forms the seal between gasket 60 and a lower end of cosmetic leg cover 34.

In the foregoing description, it will be readily appreciated by those skilled in the art that modifications may be made to the invention without departing from the concepts disclosed herein. Such modifications are to be considered as included in the following claims, unless these claims expressly state otherwise.

What is claimed is:

1. A prosthetic leg assembly comprising;

a foot and ankle portion, a foot shell having an outer surface and disposed over said foot and ankle portion and having an upper nm presenting a radially inwardly extending lip surrounding an opening, a foot gasket disposed about said opening on said rim and having a peripheral body with an outer perimeter conforming to said outer surface of said foot shell at said rim and extends under said lip to define an outwardly facing groove receiving said lip.

2. An assembly as set forth in claim 1 including a hollow boot extending upwardly from said gasket about said opening for sealing engagement with a leg portion.

3. An assembly as set forth in claim 2 wherein said gasket includes a shoulder surrounding said boot.

4. An assembly as set forth in claim 1 including an adhesive disposed on said gasket about said opening for bonding to a leg portion.

* * * * *